United States Patent [19]

Harley et al.

[11] Patent Number: 5,380,909
[45] Date of Patent: Jan. 10, 1995

[54] CAPTIVE CARBONYL HALIDE PROCESS FOR PRODUCTION OF DIARYL CARBONATES

[75] Inventors: A. Dale Harley; Craig B. Murchison; Jose Puga, all of Midland, Mich.

[73] Assignee: The Dow Chemical Company, Midland, Mich.

[21] Appl. No.: 892,395

[22] Filed: May 28, 1992

Related U.S. Application Data

[62] Division of Ser. No. 720,053, Jun. 24, 1991, abandoned.

[51] Int. Cl.$^6$ ............................................. C07C 69/96
[52] U.S. Cl. ................................................... 558/274
[58] Field of Search ........................................ 558/274

[56] References Cited

U.S. PATENT DOCUMENTS 2,444,289  6/1948  Gorin et al.
3,996,273  12/1976  Daumas
4,045,464  8/1977  Romano et al.
4,269,805  5/1981  Schoengen et al. ............. 422/106
5,167,946  12/1992  Mullins et al. ................ 558/274 X

FOREIGN PATENT DOCUMENTS 2509036  9/1976  Germany.
0164548  9/1983  Japan.
9106526  5/1991  WIPO.

Primary Examiner—Robert W. Ramsuer
Assistant Examiner—Michael G. Ambrose

[57] ABSTRACT

A process for the production of a diaryl carbonate comprising:
  contacting an aromatic hydroxy compound with a carbonyl halide in the presence of a catalyst in a reactor system under conditions sufficient for the formation of a diaryl carbonate and a hydrogen halide;
  recovering the aromatic carbonate; and
  recycling at least some of the hydrogen halide within the reactor system to regenerate the carbonyl halide.

16 Claims, 2 Drawing Sheets

CAPTIVE CARBONYL HALIDE PROCESS FOR PRODUCTION OF DIARYL CARBONATES

CROSS-REFERENCE TO RELATED APPLICATION

This is a divisional of application Ser. No. 07/720,053, filed Jun. 24, 1991, now abandoned.

The present invention relates to a process, equipment design, and method of use for the production of diaryl carbonates. More particularly the present invention relates to a reactor system for the reaction of aromatic hydroxy compounds with carbonyl halides to prepare diaryl carbonates accompanied by elimination of anhydrous hydrogen halide, which is recycled internally to regenerate the carbonyl halide.

Prior art methods for the production of diaryl carbonates have used the interfacial route involving a two phase reaction system, and various catalytic systems. The interfacial route involves the neutralization of the aromatic hydroxy compound with caustic and the subsequent reaction of an aqueous solution of the phenate type salt of the aromatic hydroxy compound with a carbonyl halide, usually phosgene. In the case where the desired product is diphenyl carbonate, excess caustic to insure the complete neutralization of phenol results in a loss of about 20% of the phosgene. Salt which represents the loss of two chlor/alkali equivalents is produced. As a consequence, the aqueous stream coming from this reaction process requires treatment prior to disposal. Caustic equivalents include the Group 1, 2, 11 and 12 hydroxides, oxides, carbonates and phosphates.

Catalytic processes to prepare diaryl carbonates have used as catalysts amines and their salts, pentavalent organophosphorous compounds and their salts and organometallic compounds. Anhydrous hydrogen chloride is produced as a side product rather than the waste salt of the interfacial route.

Examples of the foregoing processes include U.S. Pat. Nos. 2,362,865 and 3,251,873 (metal phenates), 3,234,261 (metal oxides), and 3,234,263, (tertiary amine) among others. The teachings of the foregoing United States patents are incorporated herein in their entireties by reference thereto. In U.S. Pat. No. 3,996,273 a process for manufacture of phosgene is disclosed utilizing masses of cupric chloride in contact with carbon monoxide. Despite the advance in the art in the use of $KCl/CuCl_2$ reaction masses disclosed by the reference, the need to physically move the exchange mass about the reactor system leads to solids handling problems and an energy intensive system.

Figure 1:
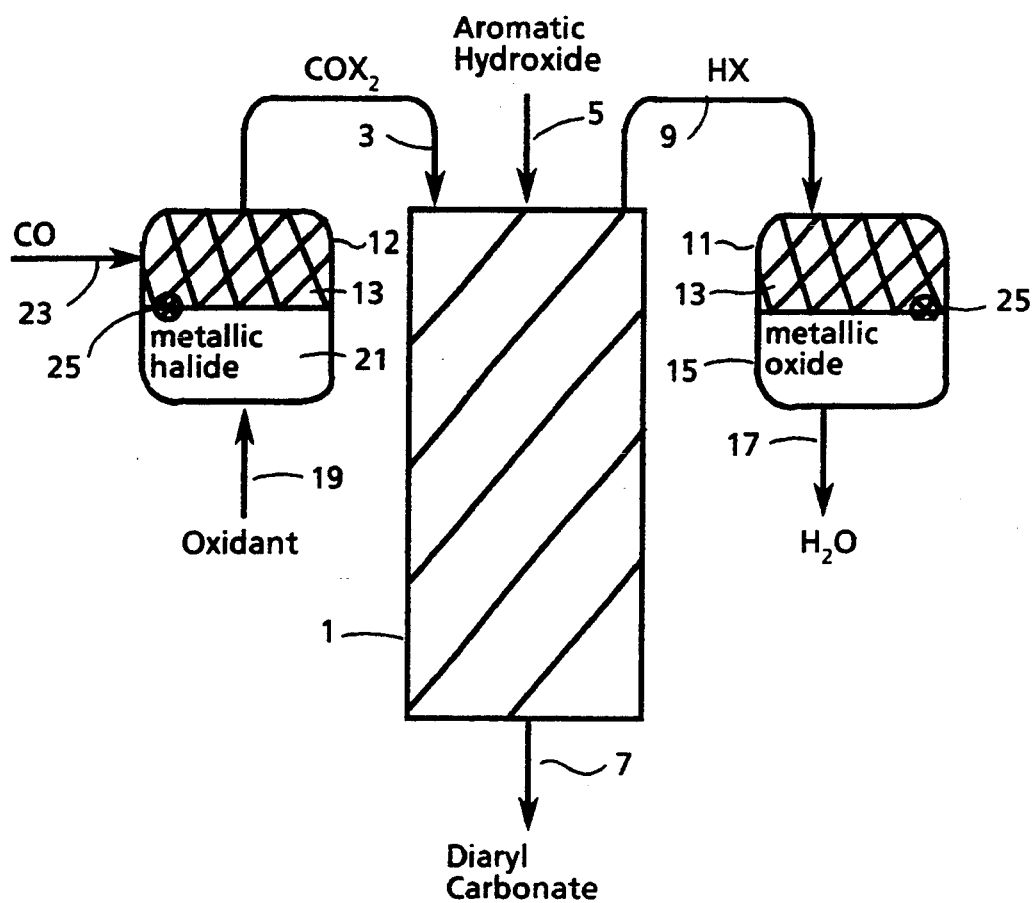
FIG. 1 contains a diagram of a twin bed dual stage reactor for the production of diaryl carbonate.

According to the present invention there is provided a process for the production of a diaryl carbonate comprising:

contacting an aromatic hydroxy compound with a carbonyl halide in the presence of a catalyst in a reactor system under conditions sufficient for the formation of a diaryl carbonate and a hydrogen halide;

recovering the diaryl carbonate; and recycling at least some of the hydrogen halide within the reactor system to regenerate the carbonyl halide.

Because the process "captures" the hydrogen halide and maintains the carbonyl halide as a captive reagent, large inventories of carbonyl halide are avoided and disposal of organic contaminated waste streams of hydrochloric acid or salt are avoided.

The use of the present invention allows for the economical production of diaryl carbonates, which are used in melt polymerization processes to produce polycarbonate resins. These polycarbonate resins are useful as molding resins in the production of shaped articles by the application of heat or other suitable techniques.

The general objective of the present invention is to avoid the disadvantages of the prior art methods of production of diaryl carbonates. These include the water and salt disposal problem associated with the interfacial method, and the problem of organic contamination of hydrogen halide streams in processes wherein byproduct hydrogen halide is separated for sale or use.

In order to achieve the benefits of the foregoing process it is desirable to employ a reactor system adapted for the production of a diaryl carbonate comprising:

1) a first reaction zone adapted for contacting carbon monoxide and a halogen selected from the group consisting of chlorine, bromine and mixtures thereof under reaction conditions to prepare a carbonyl halide;
2) a second reaction zone in operative communication with the first reaction zone adapted for contacting at least a portion of the carbonyl halide prepared in the first reaction zone with an aromatic hydroxide to prepare a hydrogen halide and a diaryl carbonate and adapted for removing at least a portion of said diaryl carbonate; and
3) a third reaction zone in operative communication with the second reaction zone adapted for contacting at least a portion of the hydrogen halide prepared in the second reaction zone with a metallic oxide compound to generate water and the corresponding metallic halide.

After substantial consumption of the metallic oxide in the third reaction zone, this reaction zone is taken off line and the process is altered. The third reaction zone is regenerated by contacting the metallic halide formed therein with an oxidant to release halogen which is supplied to the first reaction zone. A fresh metallic oxide bed is substituted for the third reaction zone until it too is in need of regeneration. If the two metal oxide/metal halide beds are of equivalent capacity, the process can repeat itself using each bed to alternately absorb hydrogen halide from the second reaction zone or to release halogen to the first zone.

In greater detail the foregoing process and reactor system are usefully employed in a method for preparing a diaryl carbonate from an aromatic hydroxide, carbon monoxide and an oxidizing agent with captive recycle of a hydrogen halide comprising:

a) contacting carbon monoxide and a halogen selected from the group consisting of chlorine, bromine and mixtures thereof in a first reaction zone under reaction conditions to prepare a carbonyl halide;
b) contacting at least a portion of the carbonyl halide from step a) with the aromatic hydroxide in a second reaction zone in operative communication with the first reaction zone to prepare a hydrogen halide and a diaryl carbonate and recovering at least a portion of the diaryl carbonate;

c) contacting at least some of the hydrogen halide produced in step b) with a metallic oxide in a third reaction zone in operative communication with the second reaction zone to generate water and the corresponding metallic halide, d) on or before exhaustion of the metallic oxide in the third reaction zone, introducing an oxidant into said third reaction zone to regenerate the metallic oxide and release halogen, and e) recycling the released halogen to step a).

Any reaction conditions and catalysts known in the prior art for the reaction of an aromatic hydroxy compound and a carbonyl halide may be suitably employed in step b) in the present process. Examples include the previously disclosed homogeneous catalyzed processes. Also suitable are tetramethyl ammonium halide catalyzed processes, disclosed in U.S. Pat. No. 3,837,555; processes catalyzed by aromatic heterocyclic basic nitrogen compounds, salts or adducts thereof, disclosed in U.S. Pat. No. 4,012,406; and activated aromatic, N-containing heterocyclic or organophosphine catalyzed reactions, disclosed in U.S. Ser. Nos. 451,893 and 451,894, both filed Dec. 18, 1989. Preferably, however, a heterogeneously catalyzed reaction is employed.

Exemplary of the heterogeneously catalyzed reactions are the processes using Lewis acids or compounds of transition metals that generate them, disclosed in U.S. Pat. No. 4,045,464. Another suitable process is the supported metal salt catalyzed process disclosed in U.S. Ser. No. 429,954, filed Oct. 30, 1989. A further suitable process utilizing $AlF_3$ catalysts is disclosed and claimed in U. S. Ser. No. 706,426, filed May 24, 1991. The teachings of the foregoing United States patents and pending applications are hereby incorporated in their entireties by reference thereto.

Catalysts comprising aluminum triflouride are particularly desired and are readily prepared by contacting an aluminum oxide such as alumina with hydrogen fluoride at elevated temperatures accompanied by evolution of water. Preferred temperatures for preparing such a catalyst are 250° C. to 700° C., more preferably 450° C. to 600° C. A preferred catalyst has a surface area from 0.1 to 1 $m^2/g$, more preferably 0.3 to 0.75 $m^2/g$. Additionally preferably the catalyst comprises from 50 to 100 percent a-aluminum trifluoride, more preferably 95 to 100 percent, and most preferably 98 to 100 percent.

Although preferred catalysts are unsupported aluminum trifluoride, the catalyst may also be incorporated onto a support if desired. For example a substrate material may be impregnated with an aluminum salt wherein the anion is an organic anion, such as a carboxylate or a dicarboxylate, for example, oxalate, or a nitrogen containing anion such as nitrate or nitrite. These salts may be converted to the corresponding aluminum oxide by calcining, for example by heating in air at temperatures above about 500° C. Conversion of the alumina coating to $AlF_3$ may then be accomplished as previously disclosed.

Suitable support materials include refractory oxides, ceramics or other inert materials which are porous and stable at high temperatures. Examples include silica, aluminosilicates, carbon, silicon carbide, aluminum nitride, silicalite, titania, zirconia etc.

The porous support material, where employed, desirably has a surface area from 50 $m^2$ per gram to 500 $m^2$ per gram. The average pore radius of the support material is desirably in the range from 50 Å to 300 Å, while the particle size of the catalyst is desirably from 25 microns to 1.5 cm. The aluminum salt prior to calcining desirably comprises 1.0 to 40 percent by weight of the catalyst, and preferably from 10 percent to about 30 percent by weight of the catalyst.

Desirable aromatic hydroxy materials for step b) are represented by the general formula:

where Ar is an aromatic or substituted aromatic group with up to 24 carbons and m is 1–3. Suitable substituents include halo or alkyl, alkadiyl, aryloxy, or alkoxy groups of 1 to 12 carbon atoms. From zero to 5 substituents may be present. Preferred aromatic hydroxy compounds are phenolic and bisphenolic compounds of up to 20 carbons. Highly preferred aromatic hydroxy starting materials are phenol, bisphenol A (2,2-di(4-hydroxyphenyl)propane) and bisphenol F (di(hydroxyphenyl)methane).

Preferred carbonyl halides are phosgene, bromophosgene and mixtures thereof. A most preferred carbonyl halide is phosgene. Aryl haloformates, which may be thought of as the intermediate product resulting from reaction of carbonyl halide and aromatic hydroxide in step b) may also be prepared by the process. They may be separated from the desired diaryl carbonate and recycled by contacting with the same or another aromatic hydroxide in one embodiment of the present invention.

As a general rule the process for step b) employs reaction conditions from 25° C. to 450° C. preferably 125° C. to 400° C. The process is desirably carried out using phosgene under conditions such that the phosgene is a gas. In a more preferable embodiment both the phosgene and aromatic hydroxide remain in the gas phase when not adsorbed on the catalyst. In one embodiment of the invention the product, diaryl carbonate, also is a gas, however, preferably it remains a liquid. The temperature ranges that are preferred depend, therefore, upon the liquid to vapor transition temperature of the reactants and the products, the pressure at which the process is carried out, and, as an upper limit, the temperature at which degradation of the product occurs. In a most preferred embodiment, where the starting materials are phenol and phosgene, and the product is diphenyl carbonate (DPC), the normal boiling point of phenol is 182° C. and that of the product diphenyl carbonate is 302° C., so the lower limit of the most preferred temperature range for the process at 1 atm is 182° C. and the upper limit is 302° C.

In a further embodiment of the invention an inert gas may be employed as a carrier gas, and the reactants and, optionally, products remain in the gas phase in step b) at temperatures below their boiling points. Desirable inert gases are nitrogen, carbon dioxide, and hydrocarbons, such as gaseous toluene. Pressures from about 0.01 atm to about 50 atm may be used in step b), with pressures from about 0.1 atm to about 5 atm being preferred.

A desirable mole ratio of the aromatic hydroxy compound to the carbonyl halide is 1:1 to 3:1. Higher ratios of carbonyl halide relative to the aromatic hydroxy compound result in larger amounts of aryl haloformate being formed. Preferred molar ratios of aromatic hydroxy compound to carbonyl halide are from 1.8:1 to 2.1:1.

The process of step b) can be carried out in any suitable reactor including a fixed bed reactor, a fluidized bed reactor or a circulating fluidized bed reactor, in which case the catalyst desirably is utilized as a fluidizable powder. Desirable residence times in such reactors are from 1 to 3000 seconds. Preferred residence times are 1 to 60 seconds. Most preferred are residence times of 1 to 10 seconds. Materials of construction must be resistant to the highly corrosive carbonyl halide. Suitable materials are glass, glass lined steel and Hastaloy TM.

For heterogeneous catalysts, periodic regeneration can improve the conversion rate of starting materials to product. Regeneration is accomplished by treating the catalyst with methanol or water at an elevated temperature in the range of about 400° C. to about 600° C.

In steps c), d) and e) the hydrogen halide byproduct is recycled by the use of metal oxide/metal halide swing reactors. In this technique two reactors or two separate regions of a single reactor are employed to alternately react the hydrogen halide produced from the phosgenation of the aromatic hydroxy compound with a metal oxide to prepare the metal halide and release water. Thereafter the metal halide is reacted with an oxidant to regenerate the metal oxide and release halogen.

A preferred metal oxide/metal halide pair for such a swing reactor system is the cupric oxide/cupric chloride system. The preferred oxidant is an oxygen containing gas, especially air. The preferred reaction conditions for converting the hydrogen halide to the corresponding metal halide are temperatures of 100° to 500° C. and pressures from atmospheric (100 kPa) to 10 atmospheres (1 MPa). The preferred reaction conditions for regenerating the metal oxide are temperatures from 50° to 500° C. and pressures from atmospheric (100 kPa) to 10 atmospheres (1 MPa).

The halogen released during the regeneration is contacted with carbon monoxide to prepare a carbonyl halide in step a). Such a process is well known in the art. Suitable reaction conditions include the use of elevated temperatures and pressures. Preferred temperatures are from 250° C. to 450° C. and pressures from atmospheric (100 kPa) to 10 atmospheres (1 MPa). Although the carbon monoxide can be introduced directly to the metal halide bed at the same time as the halogen is being generated by means of the oxidant, it is preferred to utilize a separate reaction area containing a catalyst.

A suitable catalyst for step a) has been found to be activated carbon. Any suitable form may be employed such as activated charcoal, activated bone black, etc. The activated carbon also works to absorb excess oxidant from step d) to prevent reaction of the oxidant and carbon monoxide. For its ability to perform in this dual capacity, activated carbon is a preferred catalyst for the process of step a).

It is desirable to detect the presence of oxidant in the product stream exiting the reactor during regeneration of the metal oxide bed in step d). For such purpose an oxygen sensor may be utilized such that upon sensing imminent break through of oxygen into the reactor for step a), the direction of flow is reversed.

The use of such a metal oxide/metal halide swing system is further illustrated by reference to FIG. 1 where there is illustrated a dual stage reactor system comprising primary reactor 1, supplied with carbonyl halide via line 3, and phenol via line 5. Diaryl carbonate product is removed via line 7, and hydrogen halide is routed via line 9, to one of two swing reactors, 11 and 12. Inside the reactor 11, are a layer 13, comprising, for example, activated carbon, that can act either to absorb oxygen or to catalyze the preparation of carbonyl halide, and a metallic oxide layer 15. The hydrogen halide passes through layer 13 without reaction and reacts with the metallic oxide forming a metallic halide and releasing water which is discharged via line 17. At the same time, swing reactor 12, is operating in the regeneration mode. An oxidant is supplied via line 19 to a metal halide 21 to oxidize the metal halide to the corresponding metal oxide and release halogen. The halogen enters layer 13, where it is reacted with carbon monoxide supplied via line 23, to produce the carbonyl halide which is discharged through line 3. In an alternate embodiment, the carbon monoxide may be contacted with the metal halide, 21, concurrently with the supply of oxidant. An oxygen sensor 25, placed slightly before the interface of the metal halide and absorbent layers detects imminent break through of oxygen indicating the need to reverse the direction of flow in the system. The layer, 13, is capable of absorbing oxidant should a slight break through into the layer occur.

After reversal, the operation of the twin swing reactors changes. The reactor that before had converted hydrogen halide is regenerated while supplying carbonyl halide to the primary reactor, and vice versa.

Figure 2:
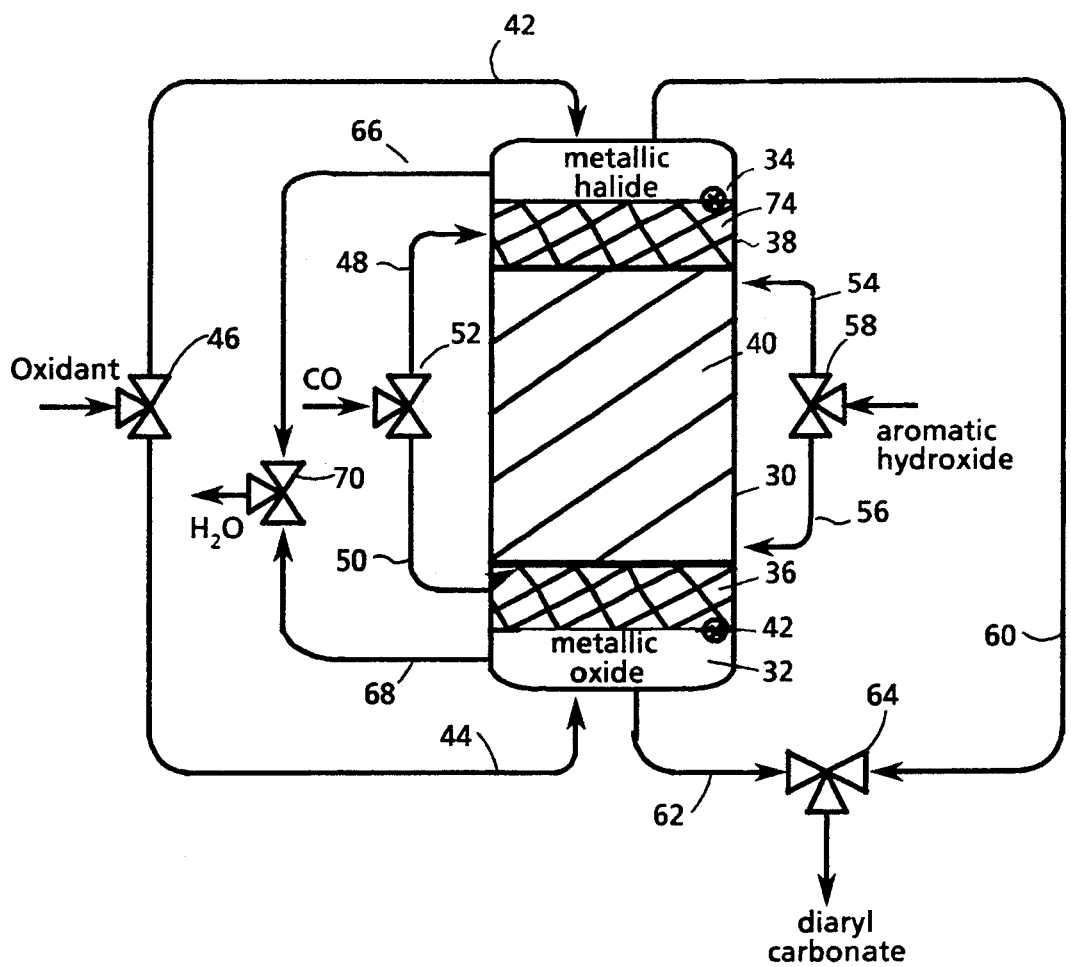
FIG. 2 contains a diagram of a multibed single stage reactor for the production of diaryl carbonate.

Instead of separate swing reactors the same benefits of the invention are obtained in a multibed single stage reactor. This reactor is illustrated in FIG. 2 and comprises reactor 30, containing at opposite ends thereof beds of metallic oxide, 32, and metallic halide 34, separated by absorbent/catalyst beds, 36 and 38, from the central reactor 40. An oxidant is introduced into the reactor either through line 42 or line 44 by means of valve 46. Similarly, carbon monoxide is introduced into the reactor in the vicinity of the absorbant/catalyst through lines 48 or 50 depending on the position of valve 52. Aromatic hydroxy compound is introduced into the reactor downstream from the absorbant/catalyst bed via lines 54 or 56 by means of valve 58. The aromatic carbonate product is removed from the reactor by lines 60 or 62 depending on the position of valve 64. Water is removed via lines 66 or 68 depending on the position of valve 70. Oxygen sensors, 72 and 74, detect imminent break through of oxidant into the absorbant/catalyst bed and cause the flow of reactants and products to reverse.

To further exemplify the operation of the embodiments of the invention it may be seen that flow of oxidant through line 42, carbon monoxide through line 48 and aromatic hydroxide through line 54 continues until oxygen sensor 74 detects imminent break through of oxidant. During this mode of operation aromatic carbonate product is removed via line 62 and water byproduct is removed via line 68. Activation of the oxygen sensor changes the state of valves 46, 52, 58, 64 and 70 so that the flow of oxidant enters the reactor via line 44, carbon monoxide enters via line 50 and aromatic hydroxide enters via line 56. Aromatic carbonate product is removed via line 60 and byproduct water is removed via line 66. Upon activation of oxygen sensor 72 the cycle is again repeated.

What is claimed is:

1. A process for the production of a diaryl carbonate comprising:
   (a) contacting an aromatic hydroxy compound with a carbonyl halide in the presence of a catalyst in a reactor system under conditions sufficient for the formation of a diaryl carbonate and a hydrogen halide;

(b) recovering the aromatic carbonate;

(c) contacting at least some of the hydrogen halide with a metallic oxide to generate a metallic halide;

(d) oxidizing the metallic halide to regenerate the metallic oxide and generate a halogen; and (e) contacting the halogen with carbon monoxide to regenerate the carbonyl halide.

2. A process according to claim 1 wherein the aromatic hydroxy compound is phenol or a bisphenol and the carbonyl halide is phosgene.

3. A process according to claim 1 wherein the metallic oxide is cupric oxide.

4. A process according to claim 1 wherein the aromatic hydroxy compound is phenol, bisphenol A or bispheonol F and the carbonyl halide is phosgene.

5. A process according to claim 1 wherein the metallic halide is oxidized with an oxygen containing gas.

6. A process according to claim 1 wherein the carbonyl halide is phosgene.

7. A process according to claim 1 wherein the hydrogen halide is contacted with the metallic oxide at a temperature from 100° to 500° C.

8. A process according to claim 1 wherein the halogen is contacted with carbon monoxide at a temperature from 250° to 450° C.

9. A process according to claim 8 wherein the halogen is contacted with carbon monoxide in the presence of an activated carbon catalyst.

10. A method for preparing a diaryl carbonate from an aromatic hydroxide, carbon monoxide and an oxidizing agent with captive recycle of a hydrogen halide comprising:

a) contacting carbon monoxide and a halogen selected from the group consisting of chlorine, bromine and mixtures thereof in a first reaction zone under reaction conditions to prepare a carbonyl halide;

b) contacting at least a portion of the carbonyl halide from step a) with the aromatic hydroxide in a second reaction zone in operative communication with the first reaction zone to prepare a hydrogen halide and a diaryl carbonate and recovering at least a portion of the diaryl carbonate;

c) contacting at least some of the hydrogen halide produced in step b) with a metallic oxide in a third reaction zone in operative communication with the second reaction zone to generate water and the corresponding metallic halide, d) on or before exhaustion of the metallic oxide in the third reaction zone, introducing an oxidant into said third reaction zone to regenerate the metallic oxide and release halogen, and e) recycling the released halogen to step a).

11. A method according to claim 10 wherein the third reaction zone alternately employs one of two twin beds comprising respectively a metallic halide or a metallic oxide reagent, said twin beds being capable of being operated sequentially to first generate water and metallic halide upon exposure of the metallic oxide reagent to a hydrogen halide and thereafter upon regeneration to generate halogen upon exposure of the metallic halide reagent to an oxidant.

12. A method according to claim 11 wherein during operation one twin bed receives hydrogen halide and generates water while the remaining twin bed receives the oxidant and generates halogen.

13. A method according to claim 12 wherein, upon nearing exhaustion of the metallic oxide in a bed, the flow of hydrogen halide and oxidizing agent is diverted to the opposite bed to reverse the operation of the twin beds.

14. A method according to claim 10 wherein the oxidant comprises an oxygen containing gas.

15. A method according to claim 14 wherein the oxidant is air.

16. A method according to claim 10 wherein the oxidant is contacted with the metallic halide at a temperature from 50° to 500° C.

* * * * *